United States Patent
Blackman et al.

(10) Patent No.: US 12,233,149 B2
(45) Date of Patent: Feb. 25, 2025

(54) SKIN CARE FORMULA, SKIN CARE PRODUCTS, AND METHODS OF MAKING THE SAME

(71) Applicant: STRYKE CLUB INC., Los Angeles, CA (US)

(72) Inventors: Stacy Blackman, Beverly Hills, CA (US); Nicole Brooks, Beverly Hills, CA (US); Darci Rosenblum, Burlingame, CA (US); Sheilagh Maguiness, Minneapolis, MN (US)

(73) Assignee: STRYKE CLUB INC., Los Angeles, CA (US)

( * ) Notice: Subject to any disclaimer, the term of this patent is extended or adjusted under 35 U.S.C. 154(b) by 0 days.

(21) Appl. No.: 17/467,955

(22) Filed: Sep. 7, 2021

(65) Prior Publication Data

US 2022/0071885 A1  Mar. 10, 2022

Related U.S. Application Data

(60) Provisional application No. 63/075,714, filed on Sep. 8, 2020.

(51) Int. Cl.

| | | |
|---|---|---|
| *A61K 8/73* | (2006.01) | |
| *A61K 8/06* | (2006.01) | |
| *A61K 8/20* | (2006.01) | |
| *A61K 8/34* | (2006.01) | |
| *A61K 8/67* | (2006.01) | |
| *A61K 9/107* | (2006.01) | |
| *A61K 33/20* | (2006.01) | |
| *A61K 47/26* | (2006.01) | |
| *A61K 47/36* | (2006.01) | |
| *A61P 17/10* | (2006.01) | |
| *A61Q 19/00* | (2006.01) | |
| *A61Q 19/10* | (2006.01) | |

(52) U.S. Cl.
CPC .................. *A61K 8/73* (2013.01); *A61K 8/06* (2013.01); *A61K 8/20* (2013.01); *A61K 8/345* (2013.01); *A61K 8/67* (2013.01); *A61K 8/737* (2013.01); *A61K 9/107* (2013.01); *A61K 33/20* (2013.01); *A61K 47/26* (2013.01); *A61K 47/36* (2013.01); *A61P 17/10* (2018.01); *A61Q 19/007* (2013.01); *A61Q 19/10* (2013.01); *A61K 2800/30* (2013.01); *A61K 2800/596* (2013.01)

(58) Field of Classification Search
None
See application file for complete search history.

(56) References Cited

U.S. PATENT DOCUMENTS

| | | |
|---|---|---|
| 4,990,334 A | 2/1991 | Longino et al. |
| 5,087,450 A | 2/1992 | Lister |
| 5,427,801 A | 6/1995 | Uehara |
| 6,121,165 A | 9/2000 | Mackey et al. |
| 6,133,166 A | 10/2000 | Nissing et al. |
| 6,544,401 B1 | 4/2003 | Colic |
| 6,589,568 B2 | 7/2003 | Camper et al. |
| 7,439,218 B2 | 10/2008 | Bowker |
| 8,318,654 B2 | 11/2012 | Hoffman et al. |
| 8,932,624 B2 | 1/2015 | Modak et al. |
| 9,066,871 B2 | 6/2015 | Anwar et al. |
| 9,074,164 B2 | 7/2015 | Rumberger et al. |
| 10,188,676 B2 | 1/2019 | Dakin |
| 10,485,827 B2 | 11/2019 | Hoover |
| 2010/0284951 A1 | 11/2010 | Pongprapansiri et al. |
| 2011/0052506 A1 | 3/2011 | Abel et al. |
| 2012/0148516 A1 | 6/2012 | Abel et al. |
| 2016/0374352 A1 | 12/2016 | Modak et al. |

FOREIGN PATENT DOCUMENTS

| | | | |
|---|---|---|---|
| BR | 102015013965 A2 | 12/2016 | |
| KR | 20050081564 A | * 1/2009 | |
| WO | WO-9409763 A1 | * 5/1994 | ............ A61K 31/00 |
| WO | 2010025293 A1 | 3/2010 | |

OTHER PUBLICATIONS

My Spice Sage, Xanthan Gum, https://www.myspicesage.com/products/xanthan-gum (Year: 2023).*
Anveya, A complete guide to diluting essential oils, https://www.anveya.com/blogs/top-tips/a-complete-guide-to-diluting-essential-oils, published Nov. 8, 2019 (Year: 2019).*
Humblebee, Guar Gum, https://web.archive.org/web/20200805185750/https://www.humblebeeandme.com/project/guar-gum/ Aug. 5, 2020 (Year: 2020).*

* cited by examiner

*Primary Examiner* — David J Blanchard
*Assistant Examiner* — Edwin Coleman Mitchell
(74) *Attorney, Agent, or Firm* — BROOKS KUSHMAN P.C.

(57) ABSTRACT

A skin-care aqueous formula includes a guar-based or xantham-based compound, glycerin, and sodium hypochlorite.

14 Claims, No Drawings

SKIN CARE FORMULA, SKIN CARE PRODUCTS, AND METHODS OF MAKING THE SAME

CROSS-REFERENCE TO RELATED APPLICATIONS

This application claims the benefit of U.S. provisional application Ser. No. 63/075,714 filed Sep. 8, 2020, the disclosure of which is hereby incorporated in its entirety by reference herein.

TECHNICAL FIELD

The present disclosure is directed to a skin care formula, products the formula may be used in, and methods of making the same.

BACKGROUND

Skin care has developed into a wide number of practices and products to support skin health, integrity, appearance, and treatment of various undesirable skin conditions. With the increasing amount of environmental and genetic-based factors which can negatively influence the wellness of people's skin, there is a growing need and demand to develop biodegradable, sustainable skin care products capable of addressing multiple skin care goals at the same time while also serving a diverse range of users.

SUMMARY

In one or more embodiments, an aqueous skin care formula is disclosed. The aqueous formula includes a combination of ingredients including sodium hypochlorite among other components. The formula may be used as an effective acne-reducing formula in a skin care product.

DETAILED DESCRIPTION

Embodiments of the present disclosure are described herein. It is to be understood, however, that the disclosed embodiments are merely examples and other embodiments may take various and alternative forms. Therefore, specific structural and functional details disclosed herein are not to be interpreted as limiting, but merely as a representative basis for teaching one skilled in the art to variously employ the present embodiments. As those of ordinary skill in the art will understand, various features illustrated and described with reference to any one of the FIGURES may be combined with features illustrated in one or more other FIGURES to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Except in the examples, or where otherwise expressly indicated, all numerical quantities in this description indicating amounts of material or conditions of reaction and/or use are to be understood as modified by the word "about" in describing the broadest scope of the present disclosure. Practice within the numerical limits stated is generally preferred. Also, unless expressly stated to the contrary: percent, "parts of," and ratio values are by weight; the description of a group or class of materials as suitable or preferred for a given purpose in connection with the present disclosure implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed.

The first definition of an acronym or other abbreviation applies to all subsequent uses herein of the same abbreviation and applies mutatis mutandis to normal grammatical variations of the initially defined abbreviation. Unless expressly stated to the contrary, measurement of a property is determined by the same technique as previously or later referenced for the same property.

It must also be noted that, as used in the specification and the appended claims, the singular form "a," "an," and "the" comprise plural referents unless the context clearly indicates otherwise. For example, reference to a component in the singular is intended to comprise a plurality of components.

As used herein, the term "substantially," "generally," or "about" means that the amount or value in question may be the specific value designated or some other value in its neighborhood. Generally, the term "about" denoting a certain value is intended to denote a range within +/−5% of the value. As one example, the phrase "about 100" denotes a range of 100+/−5, i.e., the range from 95 to 105. Generally, when the term "about" is used, it can be expected that similar results or effects according to the present disclosure can be obtained within a range of +/−5% of the indicated value. The term "substantially" may modify a value or relative characteristic disclosed or claimed in the present disclosure. In such instances, "substantially" may signify that the value or relative characteristic it modifies is within +0%, 0.1%, 0.5%, 1%, 2%, 3%, 4%, 5% or 10% of the value or relative characteristic.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4, . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits. Any two numbers, of a set of numbers, may form an integer range. For example, if the disclosed numbers are 1, 2, 3, 4, 5, the range the numbers cover may be 1 to 5, 1 to 3, 2 to 4, 3 to 4, among other options.

In the examples set forth herein, concentrations, temperature, and reaction conditions (e.g., pressure, pH, flow rates, etc.) can be practiced with plus or minus 50 percent of the values indicated rounded to or truncated to two significant figures of the value provided in the examples. In a refinement, concentrations, temperature, and reaction conditions (e.g., pressure, pH, flow rates, etc.) can be practiced with plus or minus 30 percent of the values indicated rounded to or truncated to two significant figures of the value provided in the examples. In another refinement, concentrations, temperature, and reaction conditions (e.g., pressure, pH, flow rates, etc.) can be practiced with plus or minus 10 percent of the values indicated rounded to or truncated to two significant figures of the value provided in the examples.

For all compounds expressed as an empirical chemical formula with a plurality of letters and numeric subscripts (e.g., $CH_2O$), values of the subscripts can be plus or minus 50 percent of the values indicated rounded to or truncated to two significant figures. For example, if $CH_2O$ is indicated, a compound of formula $C_{(0.8-1.2)}H_{(1.6-20.4)}O_{(0.8-1.2)}$ can be employed. In a refinement, values of the subscripts can be plus or minus 30 percent of the values indicated rounded to or truncated to two significant figures. In still another refinement, values of the subscripts can be plus or minus 20 percent of the values indicated rounded to or truncated to two significant figures.

As used herein, the term "and/or" means that either all or only one of the elements of the group may be present. For example, "A and/or B" means "only A, or only B, or both A and B". In the case of "only A", the term also covers the possibility that B is absent, i.e., "only A, but not B" and in the case of "only B", the term also covers the possibility that A is absent, i.e., "only B, but not A".

It is also to be understood that this present disclosure is not limited to the specific embodiments and methods described below, as specific components and/or conditions may, of course, vary. Furthermore, the terminology used herein is used only for the purpose of describing particular embodiments of the present disclosure and is not intended to be limiting in any way.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter. When this phrase appears in a clause of the body of a claim, rather than immediately following the preamble, it limits only the element set forth in that clause; other elements are not excluded from the claim as a whole.

With respect to the terms "comprising," "consisting of," and "consisting essentially of," where one of these three terms is used herein, the presently disclosed subject matter can include the use of either of the other two terms.

The term "one or more" means "at least one" and the term "at least one" means "one or more." The terms "one or more" and "at least one" include "plurality" as a subset.

The description of a group or class of materials as suitable for a given purpose in connection with one or more embodiments implies that mixtures of any two or more of the members of the group or class are suitable. Description of constituents in chemical terms refers to the constituents at the time of addition to any combination specified in the description, and does not necessarily preclude chemical interactions among constituents of the mixture once mixed. First definition of an acronym or other abbreviation applies to all subsequent uses herein of the same abbreviation and applies mutatis mutandis to normal grammatical variations of the initially defined abbreviation. Unless expressly stated to the contrary, measurement of a property is determined by the same technique as previously or later referenced for the same property.

A human body's largest organ, skin, is influenced by many factors on a daily basis. For example, internal factors such as genetics, age, hormones, and specific medical conditions can influence the body's skin condition. Additionally, environmental conditions such as fluctuations in temperature, humidity, wind, and/or pollutant levels, are among the many factors which also contribute to the body's skin condition. Furthermore, lifestyle choices such as personal hygiene, diet, nutritional intake, quality and quantity of water, quality and quantity of sleep, exposure to chemicals, exposure to pets, sun tanning, and various cosmetic products add a whole array of additional factors which influence the health of a person's skin.

In recent decades and years, it has been recognized that skin needs to be conditioned and taken care of for a variety of reasons including appearance, image, self-confidence, sensitivity to the various factors named above, but also overall physical and mental health and well-being. Various skin care products have been developed, but there remains to be a need for a skin care formula which would be economical, biodegradable, sustainably produced, and at the same time, delivering desirable results with respect to skin conditioning. The formula should be also applicable to a variety of skin types, serving a wide spectrum of users.

Additionally, while many skin care products have focused on the female population, there is a need to provide an effective product focused on treating male skin, especially skin of male adolescents. Due to the many physical, hormonal, cognitive, social, and emotional changes in the adolescent stages, clear skin may reduce the amount of anxiety over appearance and increase self-confidence of the maturing pre-teens and teens.

In one or more embodiments, a skin care formula is disclosed. The formula may be included in one or more products. The one or more products may include a wash, body wash, face wash, ointment, balm, lotion, face cream, body cream, shaving cream, body butter, salve, cleansing solution, rinse, scrub, face peel, after shave, wipe, moisturizer, or the like. The formula may be used to cleanse, condition, calm, soften, hydrate, revitalize, exfoliate, emolliate, treat one or more skin conditions including minimizing, diminishing, removing, and/or treating blemishes, acne, breakouts, blackheads, pimples, pustules, zits, ingrown hair, skin inflammation, removing make-up, or a combination thereof. The one or more products may be in a liquid, foam, or gel form. The one or more products may be an aqueous solution or formulation.

The formulation or formula includes one or more components. The components may be provided in one or more groups or phases. For example, the formula may include phases A, B, and/or C. Additional phases such as phase D are contemplated. The formula may include all phases A, B, C, and D. Alternatively, the formula may include at least some of the phases but exclude at least one of the phases.

Each phase of the formula may include at least one of the components or only one of the components disclosed for the specific phase named below. In other words, the formula may be free of any one or more of the components named below with the exception of water. The formula may thus include 0 wt. % of any one or more of the components named below besides the weight percentages disclosed for each component below.

The first phase A may include at least water. The water may be tap water, deionized water, distilled water, filtered water, spring water, salty water, brackish water, sea water, or a combination thereof. Water may account for the majority of the formula. Water may represent about, at least about, or at most about 50 to 80, 60 to 75, or 65 to 70 wt. % of the formula, based on the total weight of the formula. Water may represent about, at least about, or at most about 50, 52.5, 55, 57.5, 60, 62.5, 65, 67.5, 70, 72.5, 75, 77.5, or 80 wt. % of the formula, based on the total weight of the formula.

The first phase A may also include a cationic polyelectrolyte such as guar hydroxypropyltrimonium chloride, a quaternary ammonium derivative of hydroxypropyl guar or a derivatized form of guar gum which includes a hydroxypropyl group on the pendant D-galactose unit. Guar hydroxypropyltrimonium chloride is also known as guar gum, 2-hydroxy-3-(trimethylammonium)propyl ether, chloride or GHPTC. Guar hydroxypropyltrimonium chloride has the CAS number of 65497-29-2. Guar hydroxypropyltrimonium chloride is water soluble and non-pH-responsive.

Guar hydroxypropyltrimonium chloride is a biopolymer and many of its properties depend on its molecular weight and charge density, subject to cationic substitution. The degree of substitution values may range from about, at least about, or at most about 0.05 to 0.3, 0.07 to 0.25, or 0.08 to 0.2 cationic groups per anhydro sugar unit. The degree of substitution may be about, at least about, or at most about 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, or 0.30. The cationic charge density may be about, at least about, or at most about 0.2 to 1.5, 0.3 to 1.4, or 0.4 to 1.3 milliequivalents of cationic charge/gram of polymer. The cationic charge density may be about, at least about, or at most about 0.2, 0.3, 0.4, 0.5, 0.6, 0.7, 0.8, 0.9, 1.0, 1.1, 1.2, 1.3, 1.4, or 1.5 milliequivalents of cationic charge/gram of polymer. Nitrogen content, indicating the cationic charge density may be about, at least about, or at most about 1.0 to 3.0, 1.1 to 2.5, or 1.2 to 2.0%. The nitrogen content may be about, at least about, or at most about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0%.

The amount of guar hydroxypropyltrimonium chloride in the formula may be about, at least about, or at most about 0.05 to 2.5, 0.1 to 2.0, or 0.5 to 1.0 wt. %, based on the total weight of the formula. The amount of guar hydroxypropyltrimonium chloride in the formula may be about, at least about, or at most about 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 wt. %, based on the total weight of the formula. The formula may include 0 wt. % of guar hydroxypropyltrimonium chloride and thus be free of guar hydroxypropyltrimonium chloride.

Guar hydroxypropyltrimonium chloride may be configured as an antistatic agent, conditioning agent, a viscosity increasing agent. In addition to guar hydroxypropyltrimonium chloride, the formula may include other gum-based components. Among the components may be xantham gum, guar gum, or both. The gum-based components may be included, individually or in total, in an amount of about, at least about, or at most about 0.1 to 3.0 wt. %, based on the total weight of the formula. The gum-based components may be included in an amount of about, at least about, or at most about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 wt %, based on the total weight of the formula. The guar-based or xantham-based compound has nitrogen content of about 1.0 to 3.0%.

The second group of components, phase B, may include one or more surfactants and/or emulsifiers. Phase B may include surfactant(s) only. Phase B may include emulsifier(s) only. Phase B may include surfactant(s) and emulsifier(s). Phase B may be a blend of one or more compounds.

The one or more surfactants may include amphoteric surfactants or zwitterions having both positive and negative charges, or a combination thereof. In addition, or alternatively, the phase B may include one or more anionic surfactants, cationic surfactants, nonionic surfactants, or a combination thereof. Phase B may provide pH stability, degreasing, emulsifying oils and fats, suspending oils and fats, thickening, or a combination thereof. The phase B may be free of sulfates, phthalates, parabens, and/or amides. The phase B may be biodegradable. Phase B may include at least some or only components derived from plants.

The surfactants may be sulfate-free. The surfactants may include sodium lauroyl 2-methyl isethionate, dodecanoic acid, methyl-2-sulfoethyl ester, sodium salt, or sodium 2-(dodecanoyloxy)propane-1-sulfonate having the CAS number of 156572-81-5 and/or sodium lauroyl lactylate having a CAS number 13557-75-0. Sodium lauroyl 2-methyl isethionate has a chemical formula $C_{15}H_{29}NaO_5S$. Sodium lauroyl 2-methyl isethionate has a large molecular size, is water soluble, but does not penetrate skin.

The surfactants may include sodium cocoyl isethionate derived from fatty acids in coconut oil and isethionic acid. Sodium cocoyl isethionate is a biodegradable ester of isethionic acid. Sodium cocoyl isethionate is an anionic surfactant having the CAS number 61789-32-0 and a chemical formula $C_6H_{11}NaO_5S$.

Alternatively or additionally, Phase B may include sodium methyl oleoyl taurate having the CAS number 137-20-2 and a chemical formula $C_{21}H_{40}NNaO_4S$.

Phase B may additionally or alternatively include one or more glucosides. Phase B may include lauryl glucoside, coco glucoside, or both. Coco glucoside has the CAS number 141464-42-8 and chemical formula $C_{16}H_{32}O_6$. Lauryl glucoside, also called dodecyl glucoside or lauryl polyglucoside, has the CAS number 59122-55-3 and chemical formula $C_{18}H_{36}O_6$.

The group or phase B may include cocamidopropyl betaine or CAPB, which is a mixture of closely related organic compounds derived from coconut oil and dimethylaminopropylamine. CAPB has the CAS number of 61789-40-0 and a chemical formula of $C_{19}H_{38}N_2O_3$. CAPB is a fatty acid amide including a long hydrocarbon chain at one end and a polar group at the other. CAPB is a natural zwitterion having both a quaternary ammonium cation and a carboxylate.

The amount of sodium lauroyl 2-methyl isethionate, CAPB, sodium cocoyl isethionate, sodium methyl oleoyl taurate, lauryl glucoside, coco glucoside, or a combination of the one or more surfactants in the formula may be about, at least about, or at most about 1 to 30, 5 to 28, or 10 to 25 wt. %, based on the total weight of the formula. The amount of one or more surfactants individually or a total amount of the one or more surfactants in the formula may be about, at least about, or at most about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, or 30 wt. %, based on the total weight of the formula. In a non-limiting example, the amount of sodium lauroyl 2-methyl isethionate in the formula may be about, at least about, or at most about 15 to 30, 20 to 27, or 22 to 25 wt. %, based on the total weight of the formula. In a non-limiting example, the amount of CAPB may be about, at least about, or at most about 1.5 to 4, 2 to 3, or 2.2 to 2.7 wt. %, based on the total weight of the formula.

The formula may include only amphoteric surfactants. Alternatively, the formula may contain only anionic surfactants. Alternatively still, the formula may include a mixture of anionic and amphoteric surfactants. The amount of anionic surfactants may be greater than the amount of amphoteric surfactants. The ratio of the anionic surfactant to the amphoteric surfactants may be about, at least about, or at most about 5:1 to 15:1, 6:1 to 12:1, or 7:1 to 10:1. The ratio of the anionic surfactant to the amphoteric surfactants may be about, at least about, or at most about 5:1, 6:1, 7:1, 8:1, 9:1, 10:1, 11:1, 12:1, 13:1, 14:1, or 15:1.

Phase B may include one or more emulsifiers. The emulsifiers may be non-ionic emulsifiers. The emulsifiers may be water-in-oil emulsifiers. The emulsifiers may be PEG-free, referring to being free of polyethylene glycol.

The emulsifiers may include cetearyl olivate which is an ester of cetearyl alcohol and the fatty acids derived from olive oil having the CAS number of 348616-34-2. The emulsifiers may include sorbitan olivate or D-glucitol, 1,4-anhydro-, 6-monoester with olive oil fatty acids having the CAS number of 223706-40-9.

The emulsifiers may improve water and oil blending, generate liquid crystal structures similar to lipids of the outermost skin layer, contributing to moisturizing and skin barrier repairing properties of the formula.

The amount of emulsifier(s) may be, individually or a total amount of the one or more emulsifiers, about, at least about, or at most about 0.2 to 7, 0.5 to 5, or 1 to 4 wt. %, based on the total weight of the formula. The amount of emulsifier(s) may be, individually or a total amount of the one or more emulsifiers, about, at least about, or at most about 0.2, 0.3, 0.4, 0.5, 0.6, 0.7, 0.8, 0.9, 1.0, 1.25, 1.5, 1.75, 2.0, 2.25, 2.5, 2.75, 3.0, 3.25, 3.5, 3.75, 4.0, 4.25, 4.5, 4.75, 5.0, 5.25, 5.5, 5.75, 6.0, 6.25, 6.5, 6.75, or 7 wt. %, based on the total weight of the formula.

The group or phase C includes one or more salt components. Phase C includes sodium hypochlorite. Sodium hypochlorite or NaOCl includes a sodium cation and a hypochlorite anion. Sodium hypochlorite is a sodium salt of hypochlorous acid. Sodium hypochlorite may be used as a disinfectant, cleaning agent, or the like. In the formula, sodium hypochlorite may be stable or unstable. Upon decomposition, sodium hypochlorite may release chlorine. Sodium hypochlorite has the CAS number of 7681-52-9 in its anhydrous form and of 10022-70-5 as a pentahydrate. In the formula, sodium chlorite may be in its anhydrous form, pentahydrate form, or both. Sodium hypochlorite may contribute to cleansing, inflammation suppression, increased skin elasticity, skin layer thickness, the like, or a combination thereof.

Sodium hypochlorite may be included in the amount of about, at least about, or at most about 0.001 to 0.5, 0.01 to 0.25, or 0.05 to 0.12 wt. %, based on the total weight of the formula. Sodium hypochlorite may be included in the amount of about, at least about, or at most about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.11, 0.115, 0.12, 0.125, 0.13, 0.135, 0.14, 0.145, 0.15, 0.155, 0.16, 0.165, 0.17, 0.175, 0.18, 0.185, 0.19, 0.195, 0.20, 0.205, 0.21, 0.215, 0.22, 0.225, 0.23, 0.235, 0.24, 0.245, 0.25, 0.255, 0.26, 0.265, 0.27, 0.275, 0.28, 0.285, 0.29, 0.295, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, or 0.50 wt. %, based on the total weight of the formula. Non-limiting example formula includes about 0.05 wt. % sodium hypochlorite, based on the total weight of the formula. Another non-limiting example includes about 0.12 wt. % sodium hypochlorite, based on the total weight of the formula.

The formula may include one or more additional salts. Phase C may include sodium chloride, NaCl, also known as table salt which comes from mining salt deposits. The table salt may include impurities or be stripped of impurities such as magnesium, calcium, potassium, iron oxide, iron, the like, or a combination thereof. The table salt may be enriched with iodine. Phase D may include a sea salt. The sea salt may come from evaporating seawater. The sea salt may include about 0.2 to 10, 0.4 to 8, or 0.6 to 6 wt. % impurities such as magnesium, calcium, potassium salts of chloride and/or sulfate, based on the total amount of the sea salt. The sea salt may include trace amounts of other elements such as bromide, borate, strontium, silicate, fluoride, iodide, bicarbonate, the like, or a combination thereof. The amount of one or more salts may be about, at least about, or at most about 0.01 to 5, 0.1 to 2, or 0.5 to 1 wt. %, based on the total weight of the formula. The amount of one or more salts may be about, at least about, or at most about 0.01, 0.05, 0.10, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.5, 2.0, 2.5, 3.0, 3.5, 4.0, 4.5, or 5.0 wt. %, based on the total weight of the formula.

Phase C may include one or more humectants and/or emollients. Phase C may include glycerin or glycerol, a colorless, odorless, viscous liquid having a formula of $C_3H_8O_3$ and the CAS number of 56-81-85. Glycerin attracts moisture and may be used as a humectant and emollient. Glycerin may improve skin smoothness and lubrication. Glycerin may be included in the amount of about, at least about, or at most about 0.5 to 5, 1 to 2.5, or 1.5 to 2 wt. %, based on the total weight of the formula. Glycerin may be included in the amount of about, at least about, or at most about 0.5, 1, 1.5, 2, 2.5, 3, 3.5, 4, 4.5, or 5 wt. %, based on the total weight of the formula.

Phase C may include, alternatively or in addition to, at least some of the other named components, gluconolactone. Gluconolactone or glucono delta-lactone or GDL is a lactone of D-gluconic acid having the CAS number of 90-80-2 and a chemical formula of $C_6H_{10}O_6$ and is a relatively large molecule which prevents its deep penetration into the skin. Gluconolactone may be used as a skin hydrator and/or exfoliator. Gluconolactone may be included in the amount of 0.5 to 5, 1 to 2.5, or 1.5 to 2 wt. %, based on the total weight of the formula. Gluconolactone may be included in the amount of about, at least about, or at most about 0.5, 1, 1.5, 2, 2.5, 3, 3.5, 4, 4.5, or 5 wt. %, based on the total weight of the formula.

Phase C may include, alternatively or in addition to the other named components, coco-caprylate/caprate, which is a straight, unbranched wax ester made of $C_{12}$-$C_{18}$ coconut fatty alcohol and a blend of fractionated fatty acids of vegetable origin. Coco-caprylate/caprate has a non-oil character which enables its emollient function. Coco-caprylate/caprate may be included in the amount of 0.5 to 5, 1 to 2.5, or 1.5 to 2 wt. %, based on the total weight of the formula. Coco-caprylate/caprate may be included in the amount of about, at least about, or at most about 0.5, 1, 1.5, 2, 2.5, 3, 3.5, 4, 4.5, or 5 wt. %, based on the total weight of the formula.

Phase C may include components which may aid in preserving the formula and preventing the formula's deterioration such as undergoing changes in color, pH, odor, texture, consistency, etc. Such component may be disodium EDTA having a chemical formula of $C_{10}H_{16}N_2Na_2O_8$ and the CAS number of 139-33-3. Disodium EDTA is a chelating agent capable of sequestering a variety of polyvalent cations. In addition, or alternatively, potassium sorbate may be used as a preservative. Potassium sorbate is a potassium salt of sorbic acid having a chemical formula of $C_6H_7KO_2$ and the CAS number of 24634-61-5. Potassium sorbate is highly soluble in water (58.2% at 20° C.) and in water, potassium sorbate releases sorbic acid as the active ingredient. Component C may include sodium benzoate, a sodium salt of benzoic acid with a chemical formula of $C_6H_5COONa$ and the CAS number of 532-32-1.

The preservative(s) may be included, individually or in total, in an amount of about, at least about, or at most about 0.1 to 3, 0.3 to 2, or 0.5 to 1 wt. %, based on the total weight of the formula. The preservative(s) may be included, individually or in total, in an amount of about, at least about, or at most about 0.1, 0.2, 0.3, 0.4, 0.5, 0.6, 0.7, 0.8, 0.9, 2.0, 2.1, 2.2, 2.3, 2.4, 2.5, 2.6, 2.7, 2.8, 2.9, or 3.0 wt. %, based on the total weight of the formula.

The formula may include additional components such as group or Phase D. Phase D may include one or more types of oils. Phase D may include leaf oil, nut oil, root oil, seed oil, vegetable oil, or a combination thereof. Phase D may include almond oil, apricot oil, argan oil, canola oil, cashew oil, cocoa butter oil, coconut oil, corn oil, cottonseed oil, flaxseed oil, gourd oil, grapefruit seed oil, lemon oil, macadamia oil, olive oil, orange oil, palm oil, peanut oil, pecan oil, pumpkin seed oil, rapeseed oil, rice bran oil, safflower oil, sesame oil, soybean oil, sunflower oil, walnut oil, the like, or a combination thereof. The oil may be a combination of two or more oils named above. The amount of oil may be about, at least about, or at most about 0.1 to 25, 1 to 20, or 10 to 18 wt. %, based on the total weight of the formula. The amount of oil may be about, at least about, or at most about 0.1, 0.2, 03, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, or 25 wt. %, based on the total weight of the formula.

Phase D may include one or more essential oil extracts such as arborvitae, basil, *cassia*, cedarwood, chamomile, cinnamon, clary sage, clove, *eucalyptus*, Frankincense, grapefruit, hyssop, lavender, lemon, lemon grass, *melaleuca*, myrrh, orange, oregano, patchouli, peppermint, rose, rosemary, spearmint, tea tree, vetiver, ylang, or the like. The essential oil component may be a combination of two or more essential oils named above.

Alternatively or in addition, the Phase D may include one or more vitamins. Example vitamins may include one or more of vitamin C (ascorbic acid), B (thiamine, riboflavin, niacin, pantothenic acid, pyridoxine, biotin, folate, cyanocobalamin), D (cholecalciferol), E (tocopherols), K (phylloquinone), provitamin A (carotenoids), the like, a combination thereof. The vitamins may be water and/or fat soluble vitamins.

The amount of essential oil(s) and/or additional or alternative components of the Phase D may be about, at least about, or at most about 0.01 to 2.5, 0.1 to 2, or 0.5 to 1 wt. %, based on the total weight of the formula. The amount of the Phase D components may be about, at least about, or at most about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.52, 0.54, 0.56, 0.58, 0.60, 0.62, 0.64, 0.66, 0.68, 0.70, 0.72, 0.74, 0.76, 0.78, 0.80, 0.82, 0.84, 0.86, 0.88, 0.90, 0.92, 0.94, 0.96, 0.98, 1.00, 1.02, 1.04, 1.06, 1.08, 1.10, 1.12, 1.14, 1.16, 1.18, 1.20, 1.22, 1.24, 1.26, 1.28, 1.30, 1.32, 1.34, 1.36, 1.38, 1.40, 1.42, 1.44, 1.46, 1.48, 1.50, 1.52, 1.54, 1.56, 1.58, 1.60, 1.62, 1.64, 1.66, 1.68, 1.70, 1.72, 1.74, 1.76, 1.78, 1.80, 1.82, 1.84, 1.86, 1.88, 1.90, 1.92, 1.94, 1.96, 1.98, 2.00, 2.00, 2.02, 2.04, 2.06, 2.08, 2.10, 2.12, 2.14, 2.16, 2.18, 2.20, 2.22, 2.24, 2.26, 2.28, 2.30, 2.32, 2.34, 2.36, 2.38, 2.40, 2.42, 2.44, 2.46, 2.48, or 2.50, based on the total weight of the formula.

The formula may be prepared by mixing the individual phases together, adjusting pH including increasing, decreasing, and/or maintaining pH at a certain level. The formula's final pH may be acidic. The formula's final pH may be about 4.5 to 6.5, 4.8 to 6.0 or 5.0 to 5.5. The final goal or target pH of the formula may be 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, or 6.5. The method may include letting the mixture settle for an amount of time. The amount of time may be several minutes to several hours including 1 to 72 hours, 6 to 48 hours, or 12 to 24 hours. The guar-based or xantham-based compound, glycerin or gluconolactone, and sodium hypochlorite are in a ratio of about 3:5:0.5 to 5:20:1.2.

EXAMPLES

Example 1

Example 1 was prepared by charging a vessel with water of Phase A, then slowly adding Phase A powder including the guar hydroxypropyltrimonium chloride while mixing with high shear. Mixing continued for about 10 minutes, care was taken to remove any clumps. A citric acid solution was added to reduce pH of the mixture. Mixing continued while the mixture started to thicken and clarify. Speed was lowered to avoid aeration of the mixture. The Phase B components were added to the mixture, one by one. Glycerin and disodium EDTA were pre-mixed together, then added to the mixture together with the remaining C Phase components, one by one while mixing. Mixing continued until a homogenous mixture was achieved, avoiding aeration. pH was adjusted to a value within the range of 5.0 to 5.5. The homogenous mixture was allowed to settle for 24 hours, briefly mixed several times within the 24-hour interval. The mixture was used as a facial cleansing wash formula.

TABLE 1

Formula of Example 1

| Phase | Component Name | Component Amount [wt. %] |
|---|---|---|
| A | Water | 71.23 |
| A | Guar hydroxypropyltrimonium chloride | 0.50 |
| B | Sodium lauroyl 2-methyl isethionate | 22.50 |
| B | Cocamidopropyl betaine | 2.70 |
| C | Glycerin | 2.00 |
| C | Disodium EDTA | 0.30 |
| C | Sodium hypochlorite | 0.12 |
| C | Potassium sorbate | 0.15 |
| C | Sodium chloride | 0.50 |
| Total | | 100.00 |

Example 2

Example 2 was prepared by the same method as the formula of Example 1 described above according to the formula below. The formula of Example 2 was used as an anti-acne wash treatment.

TABLE 2

Formula of Example 2

| Phase | Component Name | Component Amount [wt. %] |
|---|---|---|
| A | Water | 67.50 |
| A | Guar hydroxypropyltrimonium chloride | 0.50 |
| B | Sodium lauroyl 2-methyl isethionate | 25.00 |
| B | Cocamidopropyl betaine | 3.00 |
| C | Glycerin | 2.00 |
| C | Disodium EDTA | 0.30 |
| C | Sodium hypochlorite | 0.05 |
| C | Potassium sorbate | 0.15 |
| C | Sodium chloride | 0.50 |
| C | Sea salt fragrance compound(s) | 1.00 |
| Total | | 100.00 |

Example 3

Example 3 was prepared by the same method as the formula of Example 1 described above according to the formula below. Components of the Phase D were added after the components of the Phase C were all mixed into the mixture. Example 3 was used as a facial lotion/moisturizer.

TABLE 3

Formula of Example 3

| Phase | Component Name | Component Amount [wt. %] |
|---|---|---|
| A | Water | 73.15 |
| A | Xantham gum | 0.30 |
| B | Cetearyl olivate | 5.00 |
| B | Sorbitan olivate | 0.50 |
| C | Gluconolactone | 0.50 |
| C | Sodium hypochlorite | 0.05 |
| C | Sodium benzoate | 0.50 |
| C | Coco-caprylate/caprate | 4.00 |
| D | Sunflower seed oil | 16.00 |
| Total | | 100.00 |

Example 4

Example 4 was prepared by charging a vessel with water of Phase A, then slowly adding Phase A powder including the guar hydroxypropyltrimonium chloride while mixing with high shear, Mixing continued for about 10 minutes, care was taken to remove any clumps. A citric acid solution was added to reduce pH of the mixture. Mixing continued while the mixture started to thicken and clarify, Speed was lowered to avoid aeration of the mixture. The Phase: B components were added to the mixture, one by one Glycerin and disodium EDTA were pre-mixed together, then added to the mixture together with the remaining C Phase components, one by one while mixing. Mixing continued until a homogenous mixture was achieved, avoiding aeration, pH was adjusted to a value within the range of 5.0 to 5.5. The homogenous mixture was allowed to settle for 24 hours, briefly mixed several times within the 24-hour interval. The mixture was used as a facial cleansing wash formula.

TABLE 4

Formula of Example 4

| Phase | Component Name | Component Amount [wt. %] |
|---|---|---|
| A | Water | 83.83 |
| A | Guar hydroxypropyltrimonium chloride | 0.50 |
| B | Blend of sodium lauroyl 2-methyl isethionate, cocamidopropyl betaine, sodium methyl oleoyl taurate, lauryl glucoside, and coco glucoside | 9.90 |
| B | Cocamidopropyl betaine | 2.70 |
| C | Glycerin | 2.00 |
| C | Disodium EDTA | 0.30 |
| C | Sodium hypochlorite | 0.12 |
| C | Potassium sorbate | 0.15 |
| C | Sodium chloride | 0.50 |
| Total | | 100.00 |

Example 5

Example 5 was prepared by charging a main mixing vessel with water of Phase A. In a premix vessel, glycerin and guar hydroxypropyltrimonium chloride are added and mixed until uniform. While mixing the water in the main mixing vessel, the components of the premix vessel are slowly added to the main mixing vessel to incorporate to a uniform mixture, continuing to mix to achieve uniformity, to which a clarity check is performed to ensure uniformity. Once clarity is achieved, the remaining components are added to the batch, one at a time, mixing well between each component to ensure uniform incorporation is achieved before adding the subsequent material. Then final pH and viscosity adjustments, if needed, are made. The mixture was used as a facial cleansing wash formula.

TABLE 5

Formula of Example 5

| Phase | Component Name | Component Amount [wt. %] |
|---|---|---|
| A | Water | 83.83 |
| A | Guar hydroxypropyltrimonium chloride | 0.50 |
| B | Blend of sodium lauroyl 2-methyl isethionate, cocamidopropyl betaine, sodium methyl oleoyl taurate, lauryl glucoside, and coco glucoside | 9.90 |
| B | Cocamidopropyl betaine | 2.70 |
| C | Glycerin | 2.00 |
| C | Disodium EDTA | 0.30 |
| C | Sodium hypochlorite | 0.12 |
| C | Potassium sorbate | 0.15 |
| C | Sodium chloride | 0.50 |
| Total | | 100.00 |

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the present disclosure that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. An acne-treatment composition having a formula comprising:
   more than 60 wt. % water,
   about 0.2 to 1.0 wt. % guar-based or xantham-based compound,
   about 0.5 to 1.5 wt. % gluconolactone or glycerin,
   about 5 to 28 wt. % surfactant, and
   about 0.05 to 0.12 wt. % sodium hypochlorite, the weight percentages being based on the total weight of the formula,
   the formula being sulfate, paraben, and phthalate-free.

2. The acne-treatment composition of claim 1, wherein the surfactant includes sodium lauroyl 2-methyl isethionate.

3. The acne-treatment composition of claim 1, further comprising an essential oil in the amount of about 0.01 to 2.5 wt. %, based on the total weight of the formula.

4. The acne-treatment composition of claim 1, wherein the composition includes about 10 times less sodium hypochlorite than the guar-based or xantham-based compound.

5. The acne-treatment composition of claim 1 further comprising sodium chloride in an amount of about 10 times more than sodium hypochlorite.

6. The acne-treatment composition of claim 1 having pH of about 4.5 to 6.5.

7. The composition of claim 1, wherein the composition comprises about 0.2 to 1.0 wt. % guar-based compound.

8. An acne-treatment composition having a formula comprising:
   more than 60 wt. % water,
   0.2 to 1.0 wt. % guar-based compound,
   0.5 to 1.5 wt. % gluconolactone or glycerin, and
   0.05 to 0.12 wt. % sodium hypochlorite, the weight percentages being based on the total weight of the formula,
   the formula being sulfate, paraben, and phthalate-free.

9. The acne-treatment composition of claim 1, wherein a ratio of the guar-based compound to gluconolactone or glycerin is 3:5 to 1:4.

10. The acne-treatment composition of claim 8, wherein a ratio of the guar-based compound to gluconolactone or glycerin is 3:5 to 1:4.

11. The acne-treatment composition of claim 1, wherein the guar-based or xantham-based compound has nitrogen content of about 1.0 to 3.0%.

12. The acne-treatment composition of claim 8, wherein the guar-based compound has nitrogen content of about 1.0 to 3.0%.

13. The acne-treatment composition of claim 8, further comprising a surfactant.

14. The acne-treatment composition of claim 13, wherein the surfactant is included in an amount of 10 to 25 wt. %, based on the total weight of the composition.

* * * * *